United States Patent
Rose et al.

(10) Patent No.: US 6,660,717 B1
(45) Date of Patent: Dec. 9, 2003

(54) FOLLICULOGENESIS

(75) Inventors: Ursula Maria Rose, Veghel (NL); Marcel van Duin, Newhouse (GB)

(73) Assignee: Akzo Nobel, N.V., Arnhem (NL)

( * ) Notice: Subject to any disclaimer, the term of this patent is extended or adjusted under 35 U.S.C. 154(b) by 0 days.

(21) Appl. No.: 09/856,995

(22) PCT Filed: Nov. 25, 1999

(86) PCT No.: PCT/EP99/09210

§ 371 (c)(1), (2), (4) Date: Aug. 29, 2001

(87) PCT Pub. No.: WO00/32222

PCT Pub. Date: Jun. 8, 2000

(30) Foreign Application Priority Data

Dec. 1, 1998 (EP) ............................................. 98204048

(51) Int. Cl.$^7$ ........................ A61K 38/18; A61K 38/19; A61K 38/24; C07K 14/475
(52) U.S. Cl. .......................... 514/2; 424/85.1; 530/350; 530/351; 530/397; 530/399
(58) Field of Search ............................ 424/85.1; 514/2; 530/350, 351, 397, 399

(56) References Cited

U.S. PATENT DOCUMENTS 4,196,123 A * 4/1980 Rosemberg
5,821,056 A * 10/1998 Lee

FOREIGN PATENT DOCUMENTS

| EP | 0193277 A | 3/1986 |
|---|---|---|
| WO | WO 94 15966 A | 7/1994 |
| WO | WO 95 19991 A | 7/1995 |
| WO | WO 97 31020 A | 8/1997 |
| WO | WO 98 34655 A | 8/1998 |

OTHER PUBLICATIONS

The Dictionary of Cell Biology, 1989, Lackie et al., eds. Academic Press, London, p. 83.*

Dong J. et al: "Growth Differentiation Factor–9 is Required During Early Ovarian Folliculogenesis", Nature, vol. 383, Oct. 10, 1996, pp. 531–555.

Fitzpatrick, Susan L. et al: "Expression of Growth Differentiation Factory–9 Messenger Ribonucleuic Acid in Ovarian and Nonovarian Rodent and Human Tissues", Endocrinology, vol. 139, No. 5, Nov. 14, 1997, pp. 2571–2578.

Albertini, D.F. et al: "Growth Differentiation Factor–9: A Novel TGF–β Family Member That Regulates Ovarian Follicular Development", Biology of Reproduction, (1998) vol. 58, No. Suppl. 1, pp. 133. Meeting Info.: Thirty–First Annual Meeting of the Society for the Study of Reproduction College Station, Texas, USA Aug. 8–11, 1998 Society for the Study of Reproduction.

* cited by examiner

Primary Examiner—Elizabeth Kemmerer
(74) Attorney, Agent, or Firm—Mark W. Milstead

(57) ABSTRACT

The present invention relates to the use of GDF-9 in assisted reproduction and to kits comprising GDF-9. A method is provided to stimulate follicle and oocyte development and maturation. The method comprises administering GDF-9 in combination with gonadotropins.

9 Claims, 1 Drawing Sheet

FOLLICULOGENESIS

Figure 1:
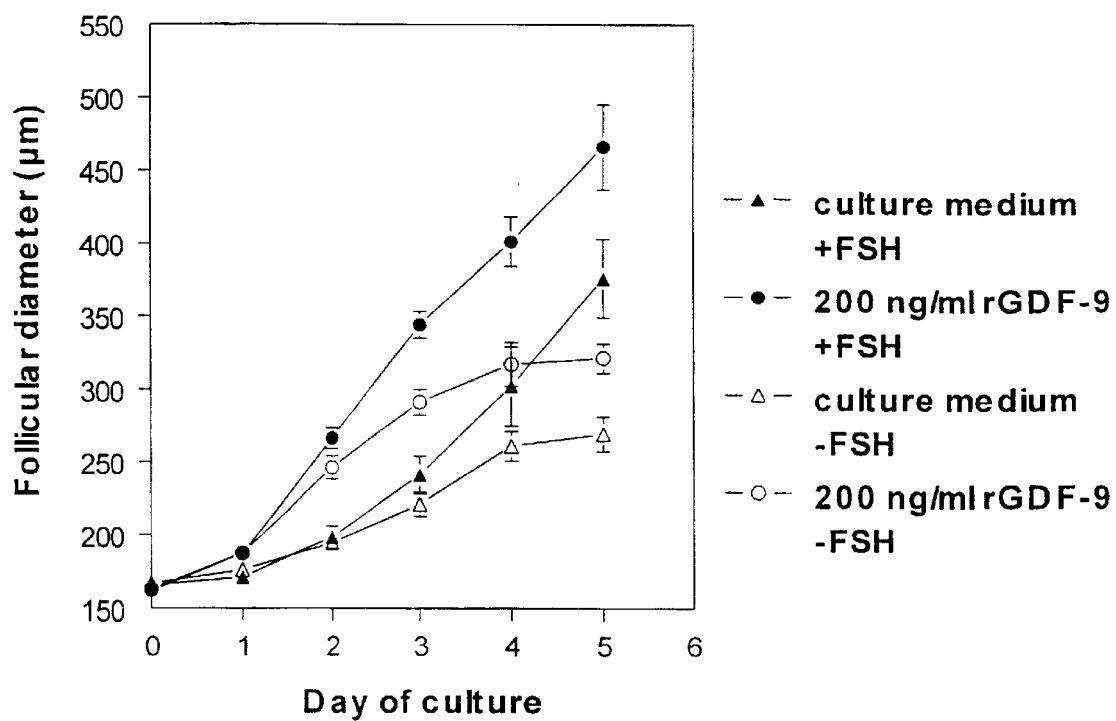

The present invention relates to the use of Growth Differentiation Factor-9 (GDF-9) in assisted reproduction and to kits comprising GDF-9.

Reproduction involves the growth and selection of ovarian follicles, leading to the ovulation of one healthy (high quality) oocyte that can be fertilised. Subsequently the fertilised oocyte develops to an embryo, which implants in a receptive endometrium and grows to a foetus and finally a healthy baby. Couples with fertility problems, however, need to undergo treatment in order to obtain children. At the moment two major treatment programs are available: Ovulation Induction (OI), for couples with female infertility due to anovulatory cycles, and In Vitro Fertilisation (IVF) for couples with either female or male fertility problems. In the case of OI protocols, low doses of gonadotropins are administered in order to induce mono-follicular growth and the ovulation of one oocyte that can be fertilised naturally. In the case of IVF relatively high levels of gonadotropins are administered in order to obtain multi-follicular development. After the induction of multi-follicular growth, oocyte maturation is induced with Luteinizing Hormone (LH)/human Chorionic Gonadotropin (hCG) and mature oocytes are retrieved by follicular puncture. After in vitro fertilisation and in vitro early embryo cleavage, 2 to 3 embryos are transferred into the uterus.

In both treatments, the gonadotropin dosing has to be adapted to individual patients in order to obtain mono- or multi-follicular development. This is extremely difficult, and success is not guaranteed. Moreover, final pregnancy outcome rates are relatively low (~20%) due to many factors, among which oocyte quality and endometrium receptivity. The cause of the relatively low success rates may lay in the way folliculogenesis and oogenesis are induced.

During the natural menstrual cycle, the gonadotropins FSH and LH induce follicle and oocyte development. Due to selection, which most likely is also controlled by FSH, only one follicle from the growing follicle pool becomes dominant and finally releases a healthy, fertilisable oocyte at ovulation. The other follicles become atretic and never will ovulate but degenerate.

It is well known that not only gonadotropins are needed for optimal follicle and oocyte development, but also growth factors. GDF-9 is such a growth factor. Its nucleotide and amino acid sequence has been described by Incerti et al (Biochim.Biophys.Acta (1994), 1222, 125–128) and McGrath et al (Mol. Endo. (1995), 9, 131–136). In GDF-9 knockout mice it has been demonstrated that follicular development ceases at the primary stage due to GDF-9 deficiency (Dong et al., 1996). Moreover it has been demonstrated that GDF-9 is present in follicles (in the oocytes to be more specific) from the primary stage up to the fully grown preovulatory stage follicles (McGrath et al., 1995). These results indicate that GDF-9 is involved in normal follicle and oocyte development.

Due to selection mechanisms only one follicle from the group of follicles that left the primordial pool, reaches the preovulatory stage, i.e. the dominant follicle, and provides a healthy, fertilizable oocyte. The others become atretic and degenerate. The mechanisms controlling the selection of a dominant follicle are not fully understood, but is the hypothesis is that the follicle that is most sensitive to FSH, is the one that becomes dominant.

Follicular growth thus is controlled by growth factors such as for example IGF-1, GDF-9, and later on by the gonadotropins FSH and LH, and by estrogens. During growth several stages can be identified: the primary stage, the preantral and antral stage, and finally the preovulatory stage.

A major difference between infertility treatment protocols and natural conception is the number of follicles and oocytes that are involved.

During Assisted Reproduction Techniques (ART) treatment, the selection mechanism that leads to the ovulation of one healthy oocyte that will be fertilised and will develop to an implanting embryo, is overruled by administration of relatively high gonadotropin (mainly FSH) doses. This protocol causes many follicles and oocytes to grow and finally many oocytes are obtained from these follicles. However, although oocyte maturation is induced with LH/CG, not all oocytes actually have matured at the moment of retrieval, or oocytes have matured but do not develop properly. In some cases, oocyte maturation can subsequently be induced in vitro, but this in vitro maturation procedure has limited success. As a result only a relatively small proportion of all oocytes obtained from the follicles will eventually develop to an embryo that implants in the endometrium. This leads to relatively low ART success.

The present invention provides for an improvement of stimulating follicle and oocyte development and maturation by administration of GDF-9 in combination with gonadotropins. This will lead to the retrieval of higher quality oocytes with higher fertilisation, cleavage and implantation capacities and thus finally to higher ART success rates. Thus, according to the present invention GDF-9 might be used in therapy. Especially, it might be used for assisted reproduction.

Thus, due to administration of GDF-9, smaller follicles, which are not destined to become apoptotic, will be selected into the growing pool, and will grow to healthy preovulatory follicles. in addition, growing follicles might be rescued by GDF-9 and will develop to a fully grown follicle with a high quality oocyte, leading to an increase in final success rates, i.e. pregnancy outcome.

The induction of follicular growth by a combination of the growth factor GDF-9 and gonadotropins might lead to a more natural follicular development, and herewith might improve oocyte quality and thus final success rate.

According to the present invention GDF-9 can be administered to female patients in order to improve follicle and oocyte development and maturation. The administration can be included in existing treatment protocols for ovarian stimulation and in vitro fertilisation. Alternatively, GDF-9 can also be used for developing isolated follicles and/or oocytes by incubation in vitro in a suitable culture medium in the presence of GDF-9, preferably in addition to FSH.

GDF-9 preferably is prepared by recombinant DNA technology in eukaryotic host cells. DNA encoding GDF-9 has been isolated and characterized and can be used for the preparation of suitable vector system. GDF-9 preferably is encoded by DNA of mammalian origin, more preferably by human DNA.

The nucleotide acid sequence of GDF-9 of one species can be used as a probe or as a source to prepare synthetic oligonucleotides to be used as primers in DNA amplification reactions allotting the isolation and identification of complete gene of other species. Using that sequence information, the complete gene can be derived from cDNA or genomic DNA from other sources or synthesized using known methods.

Under gonadotropins is to be understood FSH as isolated from human sources, such as menopausal urine. Alternatively, recombinant FSH might be prepared by production in eukaryotic host cell. Furthermore, as in current assisted reproduction protocol treatments, maturation can be induced by the administration of LH or hCG. However, also variations thereupon including GnRH antagonists and/or agonists can be used.

The proteins to be used according to the invention are those proteins which have the amino acid sequences as isolated from the relevant vertebrate tissue, and have these known sequences per se, or their allelic variants thereof.

The variations that can occur in a sequence may be demonstrated by (an) amino acid difference(s) in the overall sequence or by deletions, substitutions, insertions, inversions or additions of (an) amino acid(s) in said sequence. Amino acid substitutions that are expected not to essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Davhof, M. D., Atlas of protein sequence and structure, Nat. Biomed. Res. Found., Washington D.C., 1978, vol. 5, suppl. 3).

It is to be understood that according to the present invention also fragments of GDF-9 or splice variants can be used as long as the essential part of the protein is still intact, that is as long as the variant protein still exerts its function in follicle and oocyte development. Follicle and oocyte development can be mimicked in vitro using a mouse in vitro follicle culture system. In that system pre-antral follicles can be grown to the preovulatory stage.

The gonadotropins to be used in combination with GDF-9 according to the invention can be dimeric i.e. composed of two non-covalently bound subunits. They can, however, comprise modifications generally known in the art.

In one such modification of the gonadotropins, the C-terminus of the amino acid sequence of one of the subunits is linked, optionally through a linker moiety, to the N-terminus of the amino acid sequence of the other subunit. Preferably the linker moiety is a complete or partial CTP unit or variant thereof, or a repeated oligopeptide e.g. a 5 times repeated Ser-Gly peptide.

Another modification can be an extension of the α and/or β subunit at their respective N- or C-termninus with a complete or partial CTP unit or a variant thereof. The extension may comprise the respective CTP units in single or multiple forms. Alternatively, a complete CTP unit or partial CTP unit or multiple forms thereof can be inserted in the N- or C-termninus of said subunits. Again another modification is the introduction of one or more non-native disulfide bridges. Such extensions may also be added to GDF-9 in order to modify the half-life of the protein.

Furthermore, the proteins may be either glycosylated or partially glycosylated. Partially glycosylated proteins to be used according to the invention can be obtained by site-directed mutagenesis whereby one or more of the glycosylation recognition sites are removed. Alternatively, the glycosylation pattern can be modified by the introduction of additional glycosylation recognition sites and, optionally, the removal of one or more glycosylation recognition sites, resulting in a modified glycosylation of said proteins. A glycosylation recognition site as used herein consists of the amino acid sequence Asn-X-Ser/Thr, wherein X can be any amino acid.

As used herein, the "CTP unit" refers to the amino acid sequence found at the carboxy terminus of the β subunit of hCG which extends from amino acid 112–118 to residue 145 at the C-terminus or to a portion thereof. A "complete" CTP unit contains 28–34 amino acids, depending on the N-terminus of the CTP. A "partial" CTP unit is an amino acid sequence which occurs between positions 112–118 to 145 inclusive, but which has at least one amino acid deleted from the shortest possible complete CTP unit (amino acid 118–145). "Multiple" CTP units are understood to encompass tandem arrays of the complete CTP unit or partial CTP unit or combinations of both.

Methods to construct GDF-9 and the gonadotropins are well known in the art (Sambrook et al., Molecular Cloning: a Laboratory Manual, Cold Spring Harbor Laboratory Press, Cold Spring Harbor, latest edition). The most practical approach is to produce these proteins by expression of the DNA encoding the desired protein. Techniques for site directed mutagenesis, ligation of additional sequences, PCR, and construction of suitable expression systems are all, by now, well known in the art. Portions or all of the DNA encoding the desired proteins can be constructed synthetically using standard solid phase techniques, preferably to include restriction sites for case of ligation. Suitable control elements for transcription and translation of the included coding sequence can be provided to the DNA coding sequences. As is well known. expression systems are now available which are compatible with a wide variety of hosts. including prokaryotic hosts such as bacteria and eucaryotic hosts such as yeast, plant cells, insect cells, mammalian cells, avian cells and the like. The choice of host is particularly to post-translational events, most particularly including glycosylation. The location of glycosylation is mostly controlled by the nature of the glycosylation site within the molecule. However, the nature of the sugars occupying this site is largely controlled by the nature of the host. Most preferred hosts are from mammalian origin. Most preferably the cell is a CHO cell line. Chinese Hamster Ovary (CHO) cells have been transfected with human gonadotropin subunit genes and these cells are shown to be capable of secreting intact dimers (e.g. Keene et al (1989), J.Biol.Chem., 264, 4769–4775; Van Wezenbeek et al (1990), in From clone to Clinic (eds Crommelin D. J. A. and Schellekens H.), 245–251).

Various stimulation protocols can be applied. There are great inter- and intra-individual variations in the response of the ovaries to exogenous proteins. This makes it impossible to set a uniform dosage scheme. The dosage should, therefore, be adjusted individually depending on the ovarian response. This requires ultrasonography and monitoring of oestradiol levels. Protocols to be used for anovulation and controlled ovarian hyperstimulation are generally known. Depending on the treatment FSH administration is started at day 1, 2 or 3 and may be continued for up to 5–12 days. GDF-9 administration can be started simultaneous with FSH or 1–3 days prior to the FSH administration. The GDF-9 administration can then be stopped or continued in combination with FSH. Ovulation and/or oocyte maturation can be induced by the administration of hCG or LH. To prevent premature luteinization in addition to FSH also GnRH agonists can be administered. In patient undergoing COH premature LH surges may also be prevented by GnRH antagonist administration.

In cases where GDF-9 and FSH are jointly administered GDF-9 can be mixed with FSH, however, it might also be administered separately at approximately the same time.

Ovarian response is monitored by ultrasonography and measurement of plasma oestradiol levels. This is performed for ovulation induction as well as for COH. Typically, in case of COH, when ultrasonographic evaluation indicates the presence of at least three follicles of 16–20 mm, and there is evidence of a good oestradiol response (plasma levels of about 300–400 pg/ml (1000–1300 pmol/l) for each follicle with a diameter greater than 18 mm), the final phase of maturation of the follicles can be induced by administration of hCG. Oocyte retrieval is performed 34–35 hours later.

It is to be understood that variations of the general stimulation scheme including the uses of FSH, hCG, LH GnRH antagonists and GnRH agonists or the like are all part of this invention as long as the administration of GDF-9 is integrated in such a protocol.

Thus, according to the present invention it has been found that current infertility treatment protocols can be optimized by combined in vivo administration of GDF-9 and gonadotropins. Furthermore, initiation of follicular growth with GDF-9, followed by gonadotropin treatment, optimises follicular development and herewith oocyte quality.

The initiation of follicular growth with GDF-9 might also be followed by combined administration of GDF-9 and gonadotropins.

According to an other aspect of the invention follicles and oocytes can be developed in vitro by incubation in a chemically defined culture medium comprising GDF-9 and gonadotropins.

According to an other aspect of the invention there is provided a kit for stimulating follicle and oocyte development and maturation. Such a kit may comprise several package units. Such units may comprise GDF-9 admixed with gonadotropins. Alternatively GDF-9 and the gonadotropins might also be packaged seperately. Under gonadotropins is to be understood FSH. Optionally also separate package units might be present containing hCG or LH.

The amount of GDF-9 per ampoule might change from 10 ng–500 μg, preferably from 200 ng–200 μg. The range of FSH usually is between 50–500 IU.

For in vitro development a suitable amount of GDF-9 is an amount of 2–500 ng/ml, whereas FSH is used in range from 50 mIU–1 IU.

The pharmaceutical preparations for use according to the invention can be prepared in accordance with standard techniques such as for example are described in the standard reference, Gennaro et al. (Ed.), Remmington's Pharmaceutical Sciences, (18 th ed. Mack Publishing Company, 1990, e.g. Part 8: Pharmaceutical Preparations And Their Manufacture). For the purpose of making the pharmaceutical preparations according to the invention, the active substance is mixed with or dissolved in a pharmaceutical acceptable carrier.

Any conventional pharmaceutical carrier that does not interfere with performance of the active ingredient can be used in the preparations according to the present invention.

Pharmaceutical acceptable carriers are well known to those skilled in the art and include, for example, sterile salin, lactose, sucrose, calcium phosphate, gelatin, dextrin, agar, pectin, peanut oil, olive oil, sesame oil and water.

Furthermore the pharmaceutical composition according to the invention may comprise one or more stabilizers such as, for example, carbohydrates including sorbitol, mannitol, starch, sucrosedextrin and glucose, proteins such as albumin or casein, and buffers like alkaline phosphates.

Suitable administration routes are intramuscular injections, subcutaneous injections, intravenous injections or intraperitoneal injections, oral and intranasal administration.

LEGENDS TO THE FIGURES

FIG. 1

The effect of gonadotropins and GDF-9 on mouse follicular growth.

EXAMPLES

Example 1

Test of GDF-9 in an in vitro Follicle Culture

During follicular growth, various developmental stages are passed ranging from the primordial, primary, pre-antral, antral and finally the preovulatory stage. The proliferation and differentiation processes needed for optimal follicular development, are controlled by gonadotropins, steroids and growth factors. During infertility treatment, follicles of the early-antral stage are induced to grow with gonadotropins. This process can be mimicked in vitro using a mouse in vitro follicle culture system. In addition it is possible to start folliculogenesis in vitro at an earlier stage: the preantral or secondary stage.

Materials and Methods of the in vitro Follicle Culture

Follicle Culture

Female immature mice (F1: B6 BCA; 21–23 days of age) are anaesthetised with ether and blood is collected by means of eye extraction. After clotting, blood is centrifuged for 15 min. at 4000 g and serum is collected and stored at −20° C. until use.

Ovaries are removed and placed in Leibovitz-L15 medium (Gibco, Paisley, UK; #11415-049) supplemented with glutamin (2 mM: Gibco, #15039-019), transferrin (10 $\mu$g/ml: Sigma, St. Louis, Mo., USA; T-5391), insulin (5 $\mu$g/ml: Sigma, I-1882), ascorbic acid (50 $\mu$g/ml: Sigma, A-4034), selenium (2 ng/ml: Sigma, S-9133) and Bovine Serum Albumin (0.3%, BSA: Sigma, A-9647), at 37° C. Preantral follicles with a diameter of 150 to 180 $\mu$m are isolated with two 30 Gaugex½ needles attached to 1 ml syringes and collected in αMEM medium (Gibco, #22571-020) supplemented with glutamin (2 mM), transferrin (10 $\mu$g/ml), insulin (5 $\mu$g/ml), ascorbic acid (50 $\mu$g/ml), selenium (2 ng/ml) (i.e. αMEM culture medium) and BSA (0.3%). Isolated follicles are incubated in is a humidified incubator gassed with 5% $CO_2$ in air at 37° C. until enough follicles are isolated for the culture. From the collected follicles, follicles with normal morphological appearance i.e. a central spherical oocyte, high density of granulosa cells and a theca cell layer enclosing the entire follicle, are selected and individually cultured in Millicell-CM culture plate inserts (Millipore, Bedford, USA; #PICM 01250) with 250 $\mu$l αMEM culture medium supplemented with 5% immature mouse serum with or without GDF-9 containing human embryonic kidney 293 T cell culture supernatant. As a control, follicles are cultured with 293 T cell culture supernatant not expressing GDF-9. Follicles are subsequently cultured in a humidified incubator gassed with 5% CO, in air at 37° C. After 20 h of culture, 200 $\mu$l medium is exchanged with fresh medium in addition with 100 mU/ml recombinant human Follicle Stimulating Hormone (recFSH: NV Organon, Oss, The Netherlands) to induce follicular growth, or still without recFSH. Culture medium is exchanged every other day and the diameter of the follicles is measured each day using 100× magnification and a calibrated micrometer.

Follicular Growth

Mouse follicles of approximately 170 $\mu$m are cultured in medium with 5% immature mouse serum (IMS) and supernantant of recombinant rat GDF-9 transfected human embryonic kidney 293 T cells (200 ng/ml rGDF-9). After the first 24 h of culture, medium was refreshed and follicles were cultured further in the presence (+100 mIU/ml FSH) or absence (−FSH) of recombinant human FSH (recFSH). As a control, follicles were cultured with 20% (v/v) supernantant of non-transfected 293 T cells, also in the presence or absence of recFSH.

Under the influence of immature mouse serum and recFSH, mouse follicles grow to 350 μm within 5 days. The addition of GDF-9 to the recFSH cultures, increases follicular growth rate and follicles reach 350 μm within 3 days. After 5 days of culture, follicles reach a size of 450 μm. Also in the absence of recFSH GDF-9 increases follicular growth above the levels reached in the absence of GDF-9.

What is claimed is:

1. A follicular growth stimulating composition, comprising:

an effective amount of Growth Differential Factor-9 (GDF-9) to stimulate follicle growth and oocyte development and maturation, an effective amount of at least one gonadotropin and a pharmaceutically acceptable carrier.

2. A method for stimulating follicle and oocyte development and maturation, comprising:

administering to a female patient in need thereof an effective amount of Growth Differential Factor-9 (GDF-9) and an effective amount of at least one gonadotropin to stimulate follicle and oocyte development and maturation.

3. A follicle and oocyte development and maturation kit, comprising:

a plurality of package units comprising a mixture of at least one gonadotropin and Growth Differential Factor-9 (GDF-9).

4. A follicle and oocyte development and maturation kit, comprising:

at least one gonadotropin and Growth Differential Factor-9 (GDF-9) in separate package units.

5. A method of assisted reproduction, comprising:

administering to a female patient an effective amount of Growth Differential Factor-9 (GDF-9) and an effective amount of at least one gonadotropin to stimulate growth of follicles.

6. The method of claim 2, wherein the GDF-9 is administered prior to the administration of the at least one gonadotropin.

7. The method of claim 6, wherein the GDF-9 is begun being administered at least one day prior to the administration of the at least one gonadotropin.

8. The method of claim 5, wherein the GDF-9 is administered prior to the administration of the at least one gonadotropin.

9. The method of claim 8, wherein the GDF-9 is administered at least one day prior to the administration of the at least one gonadotropin.

* * * * *